Figure 1:
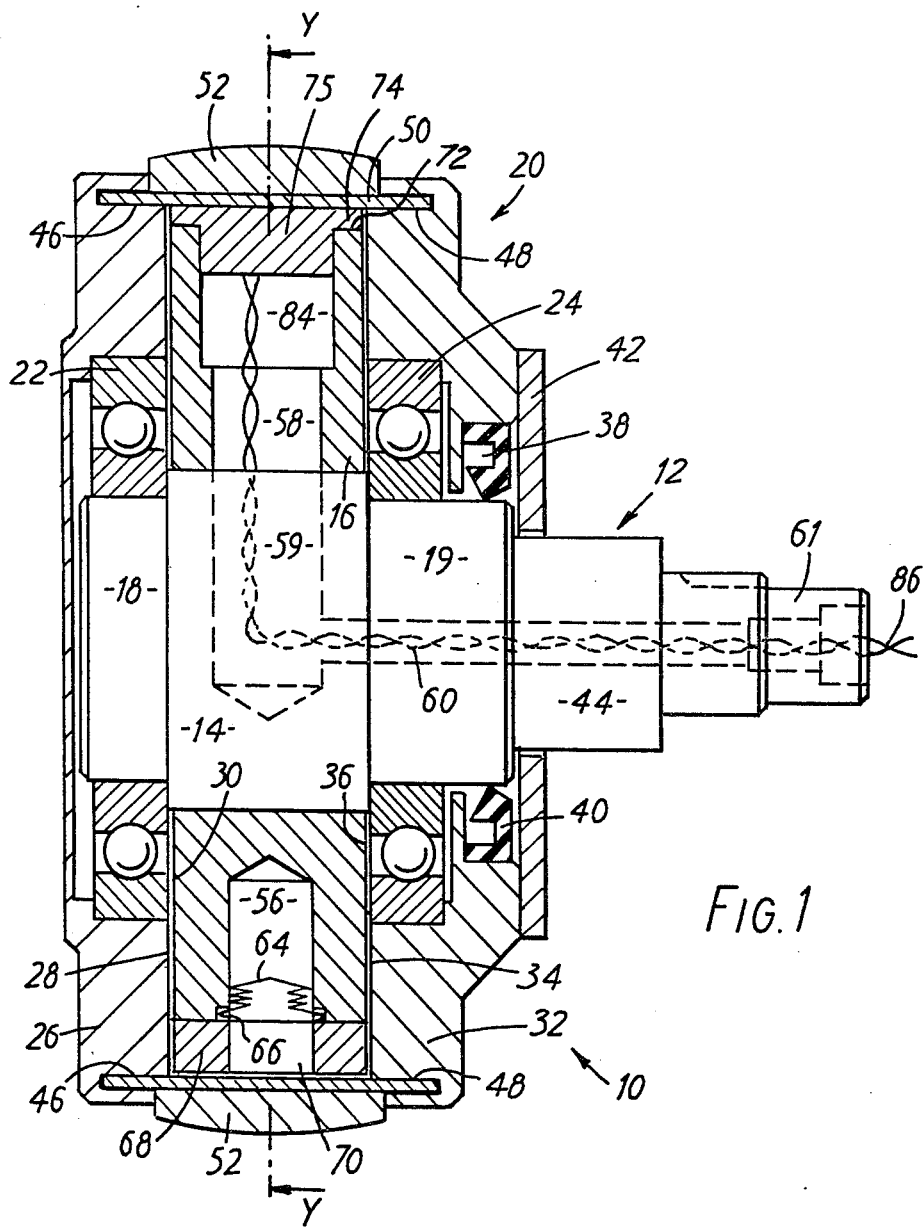

United States Patent [19]
Dickson et al.

[11] Patent Number: 4,472,974
[45] Date of Patent: Sep. 25, 1984

[54] ROLLER-TYPE ULTRASONIC INSPECTION DEVICES

[75] Inventors: John K. Dickson, Waddesdon; Trevor H. Easter, Hanslope, both of England

[73] Assignee: Schlumberger Electronics (U.K.) Limited, Hampshire, England

[21] Appl. No.: 447,580

[22] Filed: Dec. 7, 1982

[30] Foreign Application Priority Data

Dec. 8, 1981 [GB] United Kingdom ............... 8136878

[51] Int. Cl.$^3$ ............................................ G01N 29/04
[52] U.S. Cl. ................................. 73/635; 73/639; 73/146
[58] Field of Search ............... 73/635, 639, 628, 641, 73/146

[56] References Cited

U.S. PATENT DOCUMENTS

| | | | |
|---|---|---|---|
| 4,165,648 | 8/1979 | Pagano | 73/639 |
| 4,217,782 | 8/1980 | Pont | 73/639 |
| 4,302,976 | 12/1981 | Bull | 73/639 |

FOREIGN PATENT DOCUMENTS

| | | |
|---|---|---|
| 1474 | 8/1978 | European Pat. Off. . |
| 1674 | 8/1978 | European Pat. Off. . |
| 1120333 | 7/1968 | United Kingdom . |
| 1294404 | 10/1972 | United Kingdom . |

Primary Examiner—Anthony V. Ciarlante
Attorney, Agent, or Firm—Dale Gaudier

[57] ABSTRACT

A roller-type ultrasonic inspection device for inspecting vehicle tires comprises a roller assembly 20 mounted on a non-rotatable hug 16. Two piezoelectric crystals 80,82 are mounted in the hub 16 such that their principal transmitting/receiving axes A and B converge generally radially outwardly of the hub. The angle between the axes A and B is selected such that when the roller assembly 20 is urged into rolling contact with the tread-bearing surface of a tire 90, the axes meet (allowing for refraction effects) in the body of the tire beneath the tread. This ensures that the device can detect defects in the body of the tire, and is relatively insensitive to the tread.

12 Claims, 3 Drawing Figures

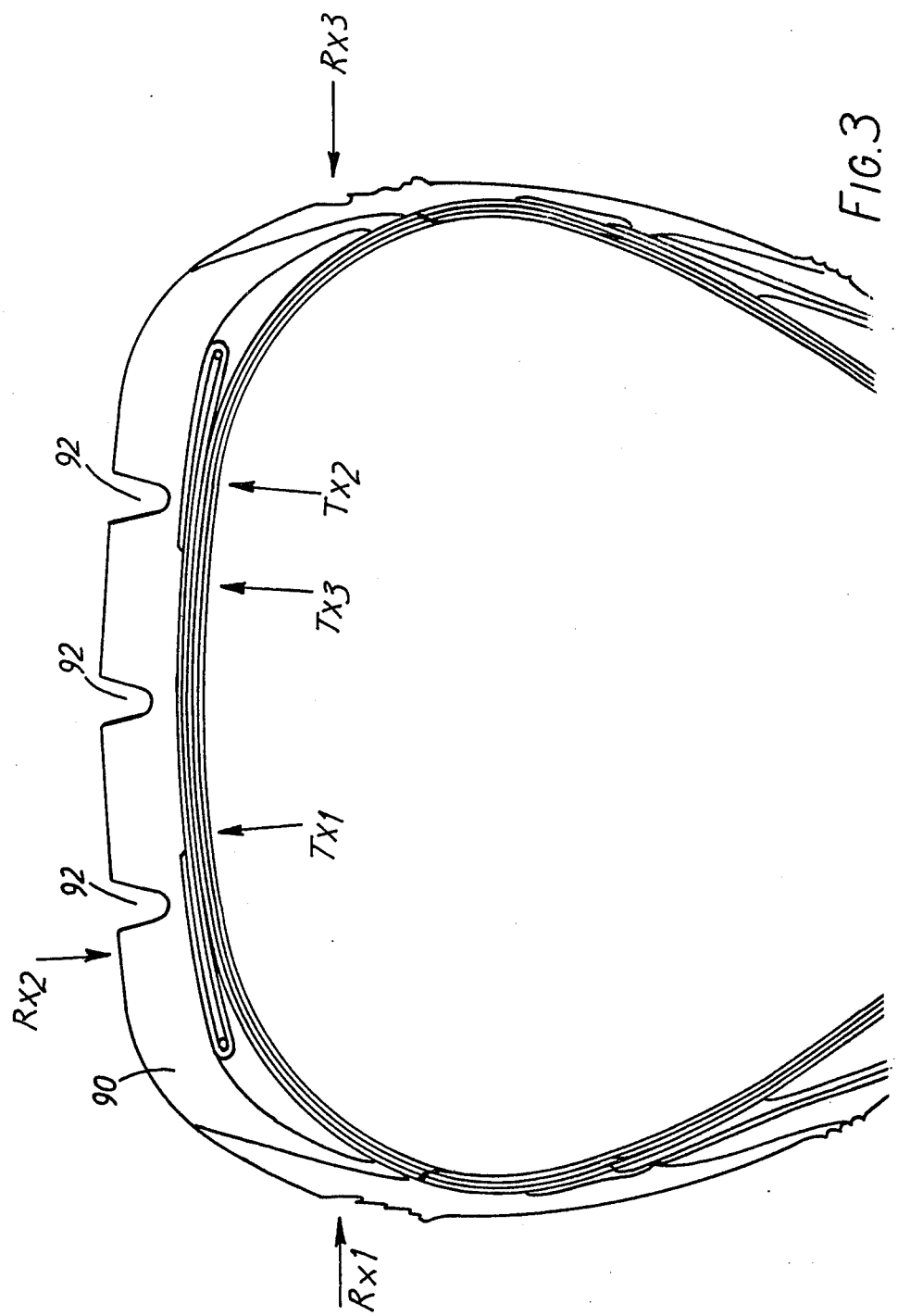

ROLLER-TYPE ULTRASONIC INSPECTION DEVICES

This invention relates to roller-type ultrasonic inspection devices, and is more particularly concerned with providing a roller-type ultrasonic inspection device which is suitable for use in the ultrasonic inspection of vehicle tires.

It is known to inspect vehicle tires ultrasonically in order to detect defects in them, particularly defects involving separation of the various layers of material making up the main body of the tire, or separation of this material from metal reinforcing wires or cords embedded in it.

In order to inspect a complete tire quickly and economically, it would be desirable to use roller-type ultrasonic probes which make rolling contact with the tire and which effect substantially continuous ultrasonic inspection of the tire as the tire is rotated through at least one complete revolution. To achieve this, it would normally be necessary for at least some of the probes to be held in contact with the radially outer surface of the tires i.e. the tread-bearing surface.

However, it has been found that conventional roller-type probes suffer from the drawback that the influence of the tread on the acoustic signal emitted or received by the probes is often substantially greater than that of the defects it is desired to detect, so that the defects cannot in practice be reliably detected. It is therefore an object of the present invention to provide an ultrasonic inspection device which can be used in a roller-type ultrasonic probe to alleviate this drawback.

According to one aspect of the present invention, there is provided a roller-type ultrasonic inspection device for inspecting a vehicle tire, the device comprising a roller member which is rotatably supported on a non-rotating hub and which is adapted to make rolling contact with the tire, and first and second ultrasonic transducers which are mounted in said hub and which each have a principal transmitting and receiving axis, said transducers being electrically connected to co-operate with each other and being mounted in said hub such that said axes converge generally outwardly of said hub, the angle between said axes being selected such that when the roller member is placed in rolling contact with the tread-bearing surface of the tire, then as a transmitter, the device tends to focus transmitted ultrasonic energy in the body of the tire beneath the tread, while as a receiver, the device is responsive to defects in the body of the tire beneath the tread.

Figure 2:
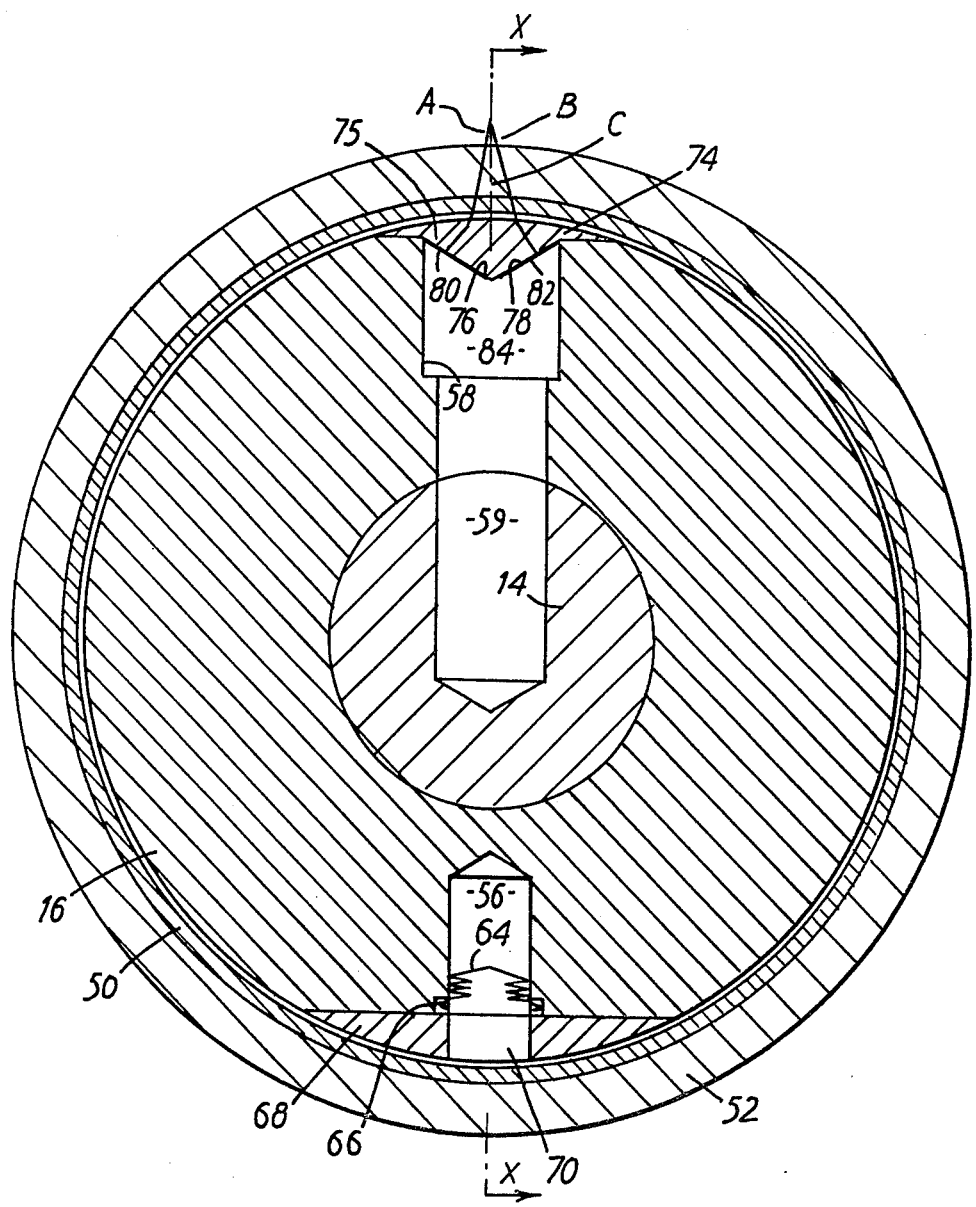

The invention will now be described, by way of example only, with reference to the accompanying drawings, of which:

FIGS. 1 and 2 are cross-sectional views of a roller-type ultrasonic probe in accordance with the present invention for inspecting vehicle tire, FIG. 1 containing the rotational axis of the probe and FIG. 2 being taken transverse to this axis; and FIG. 3 shows, somewhat diagrammatically, how a plurality of the probes of FIGS. 1 and 2 are mounted for the ultrasonic inspection of a vehicle tire.

The roller-type ultrasonic probe of FIGS. 1 and 2 is indicated generally at 10, and comprises a non-rotating, stainless steel, stepped stub axle or shaft 12, which has an enlarged diameter portion 14 on which an annular aluminium hub 16 is coaxially press-fitted. On each side of the portion 14, the shaft 12 has respective equal-diameter portions 18, 19 of lesser diameter than the portion 14, the portion 18 constituting one end of the shaft. A roller assembly 20 is rotatably mounted on the shaft portions 18, 19 by way of respective low-noise ball-bearings 22 and 24, and thus substantially completely encloses the shaft portions 14, 18 and 19 and the hub 16.

The roller assembly 20 comprises a substantially circular bearing enclosure member 26, which encloses the bearing 22 and the shaft portion 18 and has a radially extending face 28 disposed closely adjacent one radially extending face 30 of the hub 16. Additionally, the roller assembly 20 comprises an annular bearing and seal enclosure member 32, which encloses the bearing 24 and coaxially surrounds the shaft portion 19. The member 32 also has a radially extending face, which is indicated at 34 and is disposed closely adjacent the other radially extending face 36 of the hub 16. The radially inner surface of the member 32, at the axial end thereof remote from the hub 16, is shaped to define a recess 38, and a seal 40 which sealingly engages the shaft portion 19 is disposed in this recess. The recess 38 is closed by an annular seal plate 42, which is coaxially secured to the end face of the member 32 further from the hub 16. The seal plate 42 coaxially surrounds a reduced diameter portion 44 of the shaft 12, which portion 44 projects through the seal plate from the portion 19.

The members 26 and 32 are equal in diameter, and their respective faces 28 and 34 have aligned annular grooves 46, 48 machined therein. The grooves 46, 48 are coaxial with their respective members 26, 32 and each other, and the diameter of their aligned radially inner walls just exceeds the diameter of the hub 16. A tube 50 of a suitable plastics material such as that available from Du Pont under the trade name VESPEL has its opposite ends bonded in respective ones of the grooves 46, 48, and thus coaxially surrounds the hub 16 with a small annular clearance. The roller assembly 20 is completed by a tire 52 of a suitable resilient material, such as RTV 688 A & B silicone compound available from ICI Limited, which coaxially surrounds and is a tight fit on the tube 50, and is axially located on the tube by shoulders 54 defined by the radially outer walls of the grooves 46, 48.

The radially outer surface of the hub 16 contains two oppositely disposed, radially inwardly directed, cylindrical recesses 56 and 58, of which the smaller one 56 is blind. The larger recess 58 communicates, via a passage 59 extending radially through the shaft portion 14 to the centre thereof, with a passage 60 extending coaxially through the shaft portions 14, 19 and 44 to the other end 61 of the shaft 12.

The recess 56 is actually formed in a flat 62 machined on the radially outer surface of the hub 16, and is sealingly closed at its radially outer end by a stainless steel diaphragm 64. The diaphragm 64 has a rim 66 whose diameter slightly exceeds that of the recess 56, the rim being trapped in a complementarily-shaped groove in the flat 62 by a diaphragm-securing plate 68 bolted to the flat. The plate 68 contains an orifice 70 aligned with the recess 56, so that the radially outer side of the diaphragm 64 communicates with the sealed chamber defined around the hub 16 by the enclosure members 26 and 32 and the tube 50. After being bolted into position, the opposite ends of the radially outer surface of the plate 68 are machined to conform to the cylindrical radially outer surface of the hub 16.

The recess 58 is also formed in a flat machined on the radially outer surface of the hub 16, this flat being indicated at 72. A crystal mounting plate 74, which is made of aluminium and has a short protruding cylindrical portion 75 which is a press fit in the recess 58, is bonded to the flat 72 with the portion 75 disposed in the recess 58. The end of the portion 75 has two symetrically arranged, approximately semi-circular, mounting surfaces 76, 78 machined thereon, the surfaces being inclined to each other at an angle of 120° and having respective thin, flat, generally semi-circular, piezoelectric crystals 80, 82 bonded thereto. The space 84 in the recess 58 radially inwards of the two crystals 80, 82 is filled with air or other suitable gas, so that the crystals are effectively undamped. Once the plate 74 is bonded to the flat 72, its radially outer surface is machined to conform to the cylindrical radially outer surface of the hub 16.

The crystals 80, 82 are made by diametrically splitting in two a flat circular crystal of lead zirconate titanate having a resonant frequency of about 0.5 MHz, and they are electrically connected in parallel. The angle between the mounting surfaces 76, 78 is selected such that the principal transmitting/receiving axes A and B of the crystals 80, 82, which axes extend generally perpendicularly from their respective flat faces and through the mounting plate 74, converge to meet at a predetermined distance along the line C bisecting the angle between the surfaces 76, 78, for reasons which will become apparent hereinafter.

Electrical leads 86 for conveying electrical signals to and from the crystals 80, 82 extend through the space 84 in the recess 58 and the passages 59, 60 and 62 to appear from the end 60 of the shaft 12, where they are terminated in a suitable electrical connector (not shown).

The aforementioned sealed chamber defined around the hub 16 by the enclosure members 26 and 32 and the tube 50 is filled during manufacture with a combined lubricant and acoustic coupling fluid, for example glycerine. This serves not only to lubricate the bearings 22, 24 but also to provide acoustic coupling between the hub 16 and mounting plate 74 on the one hand, and the tube 50 on the other hand. The portion of the recess 56 radially inward of the diaphragm 64 is filled with air. Consequently, any increases in the volume of the fluid in the sealed chamber, e.g. due to temperature, are accommodated by movement of the diaphragm 64, which merely compresses the air radially beneath it.

In use, the roller probe 10 is spring-loaded into rolling contact with a vehicle tire to be ultrasonically inspected, by means of suitable mounting structure (not shown) to which the end 60 of the shaft 12 of the probe is secured. The mounting structure includes an adjustable bracket (not shown) by which the angular orientation of the shaft 12 and hub 16 can be adjusted by a few degrees on each side of a datum orientation in which the line C bisecting the angle between the surfaces 76, 78 passes through the point of contact of the tire 52 of the probe 10 with the vehicle tire. It will be appreciated that in the datum orientation, the crystals 80, 82 are symmetrically disposed on each side of (and closely adjacent to) the point of contact of the tire 52 with the vehicle tire. The respective principal transmitting/receiving axes A and B of the crystals 80, 82 can be regarded, after taking into consideration refraction effects at the various interfaces between the plate 74, the glycerine-filled chamber between the plate 74 and the tube 50, the tube 50, the tire 52 and the vehicle tire, as effectively meeting a predetermined depth below the surface of the object. The specified angle of 120° between the mounting surfaces 76, 78 is particularly suitable for ensuring that this predetermined depth is just below the maximum tread depth of a typical vehicle tire for a normal road vehicle such as a car. However, for other applications, different values of this angle, e.g. in the range up to 160°, can be adopted if desired.

As already foreshadowed, the probe 10 can be used either as an ultrasonic transmitter, to transmit ultrasonic energy into the vehicle tire, or as an ultrasonic receiver, to receive ultrasonic energy from the vehicle tire.

In a transmitting mode, a suitable electrical excitation signal is applied to both of the crystals 80, 82 simultaneously by way of the leads 86, causing them to emit ultrasonic energy which is coupled through the plate 74, the aforementioned acoustic coupling fluid, the tube 50 and the tire 52 into the vehicle tire. Because the crystals 80, 82 are mounted with their principal transmitting/receiving axes converging, this ultrasonic energy tends to be focussed at the point where the axes effectively meet, i.e. at the predetermined depth below the surface of the vehicle tire. Thus the effect of inhomogeneities in the surface portion of the vehicle tire above the predetermined depth, i.e. the effect of the tread, is reduced.

In the receiving mode, ultrasonic energy which has been injected into the vehicle tire by a suitable transmitter is coupled through the tire 52, the tube 50, the acoustic coupling fluid and the plate 74 to the crystals 80, 82, causing them to produce electrical output signals representative of the waveform of the received acoustic energy. These output signals are summed as a result of the parallel connection of the crystals 80, 82. Again, the convergence of the respective principal transmitting/receiving axes of the crystals 80, 82 has a focusing effect, in this case rendering the crystals responsive to energy emanating from the predetermined depth, so that the effect of the aforementioned surface inhomogeneities is again reduced.

Not only can the probe 10 be used as a transmitter or a receiver, it can also be used to form a transmitter/receiver pair either with an identical probe or with a conventional probe (e.g. a roller probe of the kind having a single flat circular piezoelectric crystal having its flat faces perpendicular to a line extending radially of its roller assembly).

An ultrasonic testing installation involving three transmitter/receiver pairs of roller probes, arranged for use in the inspection of a typical vehicle tire, is shown very diagrammatically in FIG. 3. In this installation, the transmitter probes are indicated at TX1, TX2 and TX3 and can be conventional roller probes of the kind mentioned earlier, the receiver probes are indicated at RX1, RX2 and RX3 and are all constituted by roller probes identical to the roller probe 10 of FIGS. 1 and 2, and the tire is indicated at 90 and is mounted for rotation. It will be appreciated that the receiver probes RX1, RX2 and RX3 make rolling contact with the outside surface of the tire 90, and that the receiver probe RX2 in particular rolls on the portion of the tire crossed and recrosssed by the deep grooves 92 of the main tread of the tire.

Each transmitter/receiver pair is connected to a respective one of our UFD-S ultrasonic flaw detector instruments (not shown). These instruments are broad band instruments which can be used to implement the ultrasonic testing technique known as the "shadow technique", which is described in some detail in our published U.K. Patent Application No. 2 013 344.

In operation, the tire 90 is rotated relatively slowly, while ultrasonic signals are transmitted through it. Considering just the single transmitter/receiver pair TX2 and RX2 for the sake of simplicity, the respective UFD-S instrument produces an electrical output signal consisting of repetitive bursts (i.e. pulses) each containing a relatively high frequency, which has previously been selected by tuning to cause the transmitter probe TX2 to produce an ultrasonic output signal containing a wide range of frequencies, as described in the aforementioned patent. These ultrasonic signals, after transmission through the tire 90, are received by the receiver probe RX2, which produces electrical output signals representative of the received ultrasonic signals. The output signals from the receiver probe RX2 are then applied to the UFD-S instrument, and a tunable filter (or discriminator) therein is tuned to select the most meaningful frequency band in the receiver output signal for processing (e.g. comparing with a preset threshold) and display.

If the receiver probe RX2 were a conventional roller probe, the variations in the received ultrasonic signal due to the deep grooves of the tread of the tire 90 would tend to swamp all other variations. However, because the receiver probe is constituted by a roller probe identical the probe 10, it is preferentially sensitive to changes in the ultrasonic signals emanating from beneath the tread, i.e. from within the main carcase of the tire 90. Thus the combination of the transmitter and receiver probes TX2, RX2 and the UFD-S instrument can readily be tuned to be sensitive to faults, such as layer separation, within the main carcass of the tire 90.

The rotational speed of the tire 90 is typically chosen to produce a linear speed at the point of contact with the transmitter and receiver probes in the range 0 to 18 meters/sec, which obviously permits fairly rapid inspection of the complete tire.

It will be appreciated that the transmitter probes TX1, TX2 and TX3 are energized sequentially. Thus, in an alternative arrangement, a common signal generator can be multiplexed between the three transmitter probes, and the three receiver probes can be connected via respective tunable discriminators to a multiplexer which connects each of them in turn to a suitable threshold detector. In yet another alternative arrangement, several roller probes identical to the probe 10 and operable as a plurality of transmitter/receiver pairs can be arranged to make rolling contact with the outside only of the tire 90, thus making it possible to test tires while they are actually fitted to a vehicle.

Finally, although the roller probe 10 has been described as particularly suitable for use in the ultrasonic inspection of tires, it is equally suitable for use in the ultrasonic inspection of many other objects having a rough surface or surface regions, for example heavy duty conveyor belts of the kind used for transporting coal and similar materials and of the kind used as moving walkways.

What is claimed is:

1. A roller-type ultrasonic inspection device for inspecting a vehicle tire, the device comprising a roller member which is rotatably supported on a non-rotating hub and which is adapted to make rolling contact with the tire, and first and second ultrasonic transducers which are mounted in said hub and which each have a principal transmitting and receiving axis, said transducers being electrically connected to cooperate with each other and being mounted in said hub such that said axes converge generally outwardly of said hub, the angle between said axes being selected such that when the roller member is placed in rolling contact with the tread-bearing surface of the tire and the device is operated as a transmitter, the transducers cooperate together to focus transmitted ultrasonic energy in the body of the tire beneath the tread, and when the device is operated as a receiver, the transducers are responsive to defects in the body of the tire beneath the tread.

2. A device as claimed in claim 1, wherein the first and second transducers are electrically connected in parallel.

3. A device as claimed in claim 1, wherein the first and second transducers each comprise a respective flat piezoelectric crystal.

4. A device as claimed in claim 3, wherein said crystals are substantially undamped.

5. A device as claimed in claim 3, wherein said crystals are of lead zirconate titanate.

6. A device as claimed in claim 3, wherein the first and second transducers are formed by splitting a single, substantially circular, piezoelectric crystal into two substantially symmetrical halves.

7. A device as claimed in claim 3, wherein the first and second transducers are mounted on respective flat surfaces on a common mounting member.

8. A device as claimed in claim 7, wherein said mounting member is made of aluminium.

9. A device as claimed in claim 7, wherein the included angle between said flat surfaces is less than 160°.

10. A device as claimed in claim 9, wherein said angle is about 120°.

11. A device as claimed in claim 7, wherein said mounting member is secured in a radially inwardly extending recess in said hub, with its radially outer surface machined to conform to the radially outer surface of the hub, said flat surfaces being formed on the radially inner surface of the mounting member.

12. A device as claimed in claim 11, wherein the portion of the recess radially inwardly of said transducers is gas-filled.

* * * * *